(12) United States Patent
Baralle et al.

(10) Patent No.: US 6,890,538 B1
(45) Date of Patent: May 10, 2005

(54) IMMUNIZATION AGAINST HERPES SIMPLEX VIRUS

(75) Inventors: Francisco Baralle, Trieste (IT); Juan Flo, Buenos Aires (AR); Sergio Tisminetzky, Trieste (IT)

(73) Assignee: International Centre for Genetic Engineering and Biotechnology, Trieste (IT)

( * ) Notice: Subject to any disclaimer, the term of this patent is extended or adjusted under 35 U.S.C. 154(b) by 39 days.

(21) Appl. No.: 10/048,623

(22) PCT Filed: Aug. 3, 2000

(86) PCT No.: PCT/EP00/07560

§ 371 (c)(1),
(2), (4) Date: Mar. 4, 2002

(87) PCT Pub. No.: WO01/08701

PCT Pub. Date: Feb. 8, 2001

(30) Foreign Application Priority Data

Aug. 3, 1999 (GB) ............................................. 9918283

(51) Int. Cl.[7] ............................................ A61K 39/245
(52) U.S. Cl. ............................... 424/229.1; 424/184.1; 435/6
(58) Field of Search ............................. 435/320.1, 480, 435/641, 472, 6; 424/229.1, 184.1, 93.21, 93.4, 93.2

(56) References Cited

U.S. PATENT DOCUMENTS 5,877,159 A 3/1999 Powell et al.
6,150,170 A * 11/2000 Powell et al. ............... 435/455

FOREIGN PATENT DOCUMENTS

| WO | WO 96/34631 | * 11/1996 |
|----|----|----|
| WO | WO 98/44131 | 10/1998 |
| WO | WO 99/18221 | * 4/1999 |

OTHER PUBLICATIONS

Flo et al. Vaccine, 2001, vol. 19, pp. 1772–1782.*

Medina et al , Vaccine, 2000, vol. 19, pp. 1573–1580.*

Fennelly et al, "Mucosal DNA Vaccine Immunization Against Measles with a Highly Attenuated *Shigella flexneri* Vector", The Journal of Immunology 162:1603–1610 (1999).

Karem et al, "Protective Immunity Against Herpes Simplex Virus (HSV) Type 1 Following Oral Administration of Recombinant *Salmonella Typhimurium* Vaccine Strains Expression HSV Antigens", Journal of General Virology 78:427–434 (1997).

Okada et al, "Intranasal Immunization of a DNA Vaccine with IL–12– and Granulocyte–Macrophage Colony–Stimulating Factor (GM–CSF)–Expressing Plasmids in Liposomes Induces Strong Mucosal and Cell–Mediated Immune Responses Against HIV–1 Antigens", Journal of Immunology 157(7):3638–3647 (1997).

Kuklin et al, "Role of Mucosal Immunity in Herpes Simplex Virus Infection", The Journal of Immunology 160:5998–6003 (1998).

Paglia et al, "Gene Transfer in Dendritic Cells, Induced by Oral DNA Vaccination With *Salmonella typhimurium*, Results in Protective Immunity Against a Murine Fibrosarcoma", Blood 92:3172–3176 (1998).

Darji et al, "Oral Somatic Transgene Vaccination Using Attenuated S. typhimurium", Cell 91:765–775 (1997).

Kuklin et al, "Induction of Mucosal Immunity against Herpes Simplex Virus by Plasmid DNA Immunization", Journal of Virology 71(4):3138–3145 (1997).

Bourne et al, "DNA Immunization against Experimental Genital Herpes Simplex Virus Infection", The Journal of Infectious Diseases 173:800–807 (1996).

Bourne et al, "DNA immunization confers protective immunity on mice challenged intravaginally with herpes simplex virus type 2", Vaccine 14(13):1230–1234 (1996).

Sizemore et al, "Attenuated *Shigella* as a DNA Delivery Vehicle for DNA–Mediated Immunization", Science 270:299–302 (1995).

Bernstein and Stanberry, "Herpes simplex virus vaccines", Vaccine 17:1681–1689 (1999).

Chabalgoity et al, "A *Salmonella typhimurium htrA* live vaccine expressing multiple copies of a peptide comprising amino acids 8–23 of herpes simplex virus glycoprotein D as a genetic fusion to tetanus toxin fragment C protects mice from herpes simplex virus infection", Molecular Microbiology 19(4):791–801 (1996).

Manickan et al, "Genetic Immunization Against Herpes Simplex Virus—Protection Is Mediated by CD4+ T Lymphocytes", The Journal of Immunology 155:259–265 (1995).

(Continued)

*Primary Examiner*—Ali R. Salimi
(74) *Attorney, Agent, or Firm*—Nixon & Vanderhye P.C.

(57) ABSTRACT

The invention relates to a vaccine against herpes simplex virus (HSV) comprising an invasive but attenuated or non-pathogenic bacterium, which bacterium comprises a coding sequence encoding a HSV antigen in a form that enables said coding sequence to be transferred to a host cell of a human or animal host which the bacterium is capable of invading and to be expressed in said cell to form said antigen without the introduction of an antimicrobial agent to lyse the bacterium. The invention also provides similar vaccines against other viruses.

24 Claims, 5 Drawing Sheets

OTHER PUBLICATIONS

McClements et al, "Immunization with DNA vaccines encoding glycoprotein D or glycoprotein B, alone or in combination, induces protective immunity in animal models of herpes simplex virus–2 disease", Proc. Natl. Acad. Sci. USA 93:11414–11420 (1996).

McDermott et al, "T Lymphocytes in Genital Lymph Nodes Protect Mice from Intravaginal Infection with Herpes Simplex Virus Type 2", The Journal of Infectious Diseases 159(3):460–466 (1989).

McClements et al, "The prophylactic effect of immunization with DNA encoding herpes simplex virus glycoproteins on HSV–induced disease in guinea pigs", Vaccine 15(8):857–860 (1997).

Gallichan and Rosenthal, "Specific secretory immune responses in the female genital tract following intranasal immunization with a recombinant adenovirus expressing glycoprotein B of herpes simplex virus", Vaccine 13(16):1589–1595 (1995).

* cited by examiner

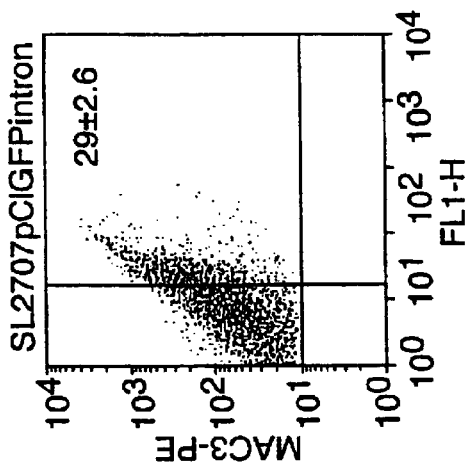
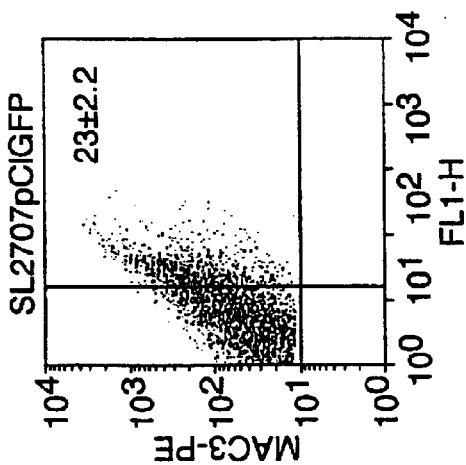
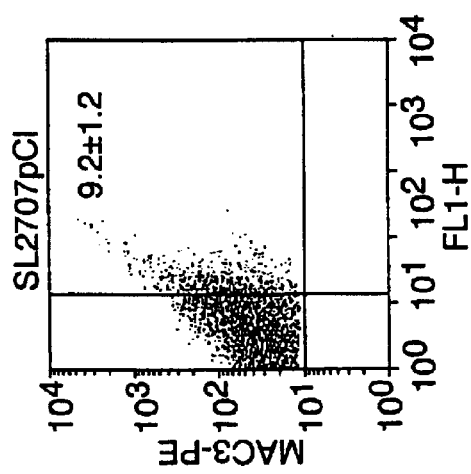
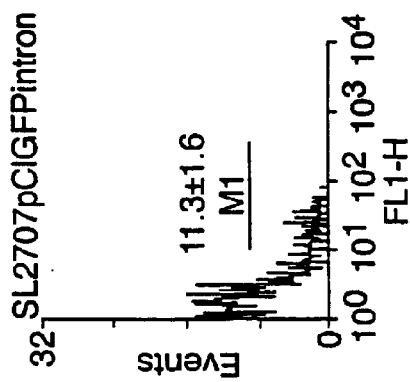
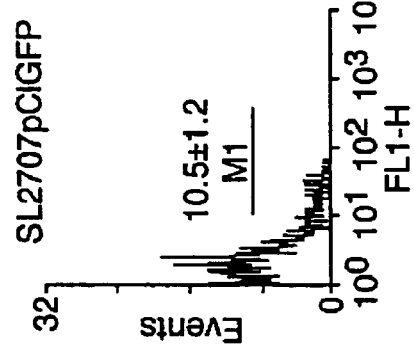
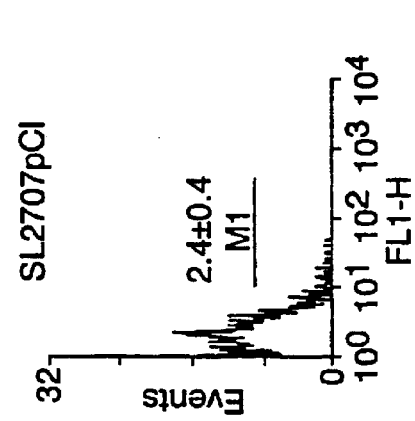

IMMUNIZATION AGAINST HERPES SIMPLEX VIRUS

This application is the US national phase of international application PCT/EP00/07560 filed 3 Aug. 2000, which designated the US.

FIELD OF THE INVENTION

The invention relates to vaccines, especially prophylactic vaccines, against Herpes Simplex Virus (HSV)-mediated disease and other viral diseases.

BACKGROUND OF THE INVENTION

As noted in Bernstein and Stanberry (1999) in a recent review and discussed more extensively there and in the references cited therein, herpes simplex viruses type 1 and 2 (HSV-1 and HSV-2) are common throughout the world. They produce not only a primary infection but also latent and recurrent infections. HSV can cause a variety of clinical illnesses including genital herpes, oral-facial infections (e.g. gingivosto-matitis, labialis, pharyngitis), cutaneous infections (e.g. whitlow, herpes gladatorium), ocular infections, neonatal herpes, herpes encephalitis, disseminated infection and erythema multiforme.

The severity and duration of most symptomatic primary infections can be reduced by antiviral therapy but this does not generally affect the establishment of latency or reduce recurrence.

Similarly, treatment of recurrent infections can decrease the severity of the disease and daily suppressive therapy can decrease both symptomatic and asymptomatic recurrences, but treatment does not affect latency and the effect is lost when therapy is discontinued. The life-long nature of this infection, the increasing prevalence of genital herpes despite the availability of effective antiviral therapies and the severity of the disease in neonates and the immunocompromised make HSV an important target for vaccine development. However, no effective vaccine is yet available (Bernstein et al, 1999).

A distinction needs to be drawn between prophylactic and therapeutic vaccines. As discussed by Bernstein et al (1999) the aims for a prophylactic, preventative, vaccine are to prevent acute clinical disease, viral infection and viral replication in the genital tract, and to prevent or reduce the establishment of latency and subsequent recurrences of the disease, either symptomatic or asymptomatic. Ideally, such a vaccine would provide a broad and durable "sterilising immunity" at the points of entry of the virus into the body, e.g. the genital tract, nasal and oro-pharingeal mucosa and the eye. This would eliminate the virus at the entry point before .3replication or entry into the peripheral nervous system. Naturally, such a prophylactic vaccine is highly desirable as it would prevent infection rather than merely treating an established infection. That is generally true for any vaccine but a prophylactic vaccine is all the more desirable in case of HSV-mediated disease because of HSV's ability to establish latency and give rise to recurrent infections.

By contrast, therapeutic vaccines are aimed at treating patients who have an established latent infection. Thus, they are intended to reduce clinical recurrences of the disease and to reduce viral shedding. (Shedding is the phenomenon by which viruses are released from the genital tract, possibly in the absence of disease symptoms, leading to transmission of HSV disease to previously unaffected individual. Thus, in addition to treating the individual in question, therapeutic vaccines are intended to prevent further spread of HSV-mediated disease.)

Bernstein et al (1999) identify six possible types of HSV vaccine. These are: (i) inactivated virion vaccines, (ii) recombinantly produced virion components or subunits (i.e. proteins), (iii) live genetically attenuated HSV mutants, (iv) replication-deficient HSV mutants, (v) live vected vaccines expressing HSV antigens, and (vi) DNA vaccines.

Virion-based vaccines (i) have not proved effective against HSV and have several drawbacks, e.g. problems with providing consistent concentrations of immunogens, ensuring that all virus is inactivated, eliminating potentially oncogenic viral contaminant DNA and high production costs.

Subunit vaccines (ii) are considered safer but less effective at inducing cell mediated responses. Subunit vaccines have had some success in the treatment of experimental recurrent genital herpes and in the reduction of viral shedding but this strategy has not yet been successfully applied to prophylactic, as opposed to therapeutic, vaccines.

Attenuated live virus vaccines (iii) have similarly been unsuccessful. Generally, live viral vaccines are developed by repeatedly passaging virus in cell culture until the virus becomes less virulent. This has not worked for HSV, where passaging in cell culture does not result in stable attenuation, such that passaged HSV strains have the potential to regain full virulence. Defining and eliminating specific genes involved in viral latency or reactivation has also been attempted. One candidate gene was the thymidase kinase (Tk) gene. An HSV-2 vaccine was developed which was protective in experimental challenge systems but proved to be poorly immunogenic in phase 1 trials and thus not effective. Deletion of the gamma 34.5 gene (ICP 34.5), believed to be central to neurovirulence, appears to diminish virulence and to increase but maybe not eliminate latency and reactivation.

Replication deficient HSV mutants (iv) have been used in the treatment of experimental recurrent genital herpes in guinea pigs but no effective prophylactic vaccine has been designed using this strategy.

Live vectored vaccines (v) have also been investigated. In a live vectored vaccine, one or more HSV genes are inserted into a replication-competent viral or bacterial vector, such as an adenovirus. Following immunisation, the vector replicates and expresses immunogenic proteins. Possible vectors include vaccinia viruses, varicella-zoster viruses, adeno-associated viruses and the bacterium *Salmonella typhimurium*. This approach is exemplified by Chabalgoity et al (1996) and Karem et al (1997).

DNA vaccines (vi) have also had only limited success. There are some reports indicating that intramuscular immunisation with a plasmid carrying a gene encoding HSV antigen (glycoprotein D or B) under the control of a eukaryotic promoter is effective to induce protection in mice and guinea pigs against an intravaginal challenge with the virus. However, these studies also make it clear that these vaccines are ineffective in actually preventing infection. Attempts to induce protective mucosal immunity by administering DNA intranasally have similarly shown poor results in preventing infection despite eliciting production of high titers of specific IgA antibodies.

Accordingly, it can be seen that no truly prophylactic vaccine is yet available, in the sense that no vaccine is yet available that prevents viral invasion. If viral invasion cannot be prevented, latency can be established and recurrent disease may result. This is particularly serious for infants born to infected mothers suffering recurrent disease.

Clearly, there is therefore a need to develop prophylactic HSV vaccines. Currently, there is no effective prophylactic HSV vaccine and the prevalent idea is that immunity to HSV is seldom if ever adequate to prevent viral invasion. For example, Bernstein et al (1999) indicate that they do not consider the induction of a durable sterilising immunity, especially in the genital tract, to be feasible at this time. As a result, their view is that prophylactic HSV vaccines in humans should not be expected to prevent infection completely but only to provide protection against clinical signs and symptoms of HSV infection.

SUMMARY OF THE INVENTION

Against this background, we have, surprisingly, identified a strategy for the development of an effective prophylactic HSV vaccine.

Recently, it has been reported the use of attenuated strains of Shigella and Salmonella as vehicles to deliver plasmid DNA in vivo into eukaryotic cells (Sizemore et al, 1995; Darji et al, 1997; Paglia et al, 1998; Fennelly et al, 1999). U.S. Pat. No. 5,877,159 (Powell/University of Maryland at Baltimore, 2 Mar. 1999) also provides similar findings. However, U.S. Pat. No. 5,877,159 does not provide any data showing protection against HSV. In particular, it provides no means by which a specific mucosal immune response against HSV can be obtained. Here, we show that the use of such an attenuated strain of Salmonella to transfer the HSV glycoprotein gene is effective to induce protection against an intravaginal challenge. This forms the basis of a strategy to develop a prophylactic vaccine against HSV.

Furthermore, we have definitively demonstrated that the immunity obtained is due to the transcription of the protein by a eukaryotic nuclear process, probably in macrophages and dendritic cells, and not by the expression of the protein by the invading bacteria This is a point of fundamental importance when an intracellular bacterium is used to deliver DNA to eukaryotic cells. The other possibility is that the protein is produced by the invading bacteria themselves by an unspecific initiation of the transcription under the control of a cryptic promoter. In other reports using this technique in non-HSV systems, reporter genes (beta galactosidase or GFP) were put under the control of prokaryotic or eukaryotic promoters (Darji et al, 1997; Paglia et al, 1998). In these reports, the absence of activity when a prokaryotic promoter was used was taken as an indication that the synthesis of the protein was due to eukaryotic events. Furthermore, by means of RT-PCRT, the removal of an intron placed in a non-coding region was demonstrated in a small fraction of RNA (Darji et al, 1997).

To demonstrate rigorously that the totality of the protein produced was derived from a eukaryotic nuclear process we introduced an intron in the GFP. We found similar levels of expression of the GFP in peritoneal macrophages after the intraperitoneal inoculation of salmonellae harboring the GFP plasmid with or without the intron. Furthermore, after the oral administration we found transfected macrophages in the Peyer patches, lamina propria of the small intestine and in the spleen. This is the first time that expression has been conclusively demonstrated to occur only in the cells of the eukaryotic host.

In addition, the distinction between the techniques of the present invention and those of Chabalgoity et al (1996) and Karem et al (1997) should be noted. In those studies, *S. typhimurium* was used as a vector to deliver HSV-1 antigens to an organism. However, crucially, expression took place in the bacterium, rather than by transfer to the eukaryotic cells of the host.

Further, WO 98/44131 (Walter Reed Army Institute of Research) describes a method whereby attenuated Shigella are transformed with DNA encoding antigens and allowed to enter baby hamster kidney (BHK) cells. Antimicrobial agents are then introduced to lyse the attenuated bacteria such that the antigen-encoding DNA is released into the cells. The present invention does not require the use of such lytic antimicrobial agents. Rather, the antigen-encoding DNA is transferred without any need for external lytic agents to be introduced.

We have shown that Salmonella-based DNA immunisation with expression of antigens taking place in the cells of the mammalian host is an effective method to induce a protective mucosal and systemic cellular immune response against HSV infection. In other reports where DNA from plasmids carrying the gD gene was administered by the intramuscular route, the humoral immune response was mainly tested, and even though protection after an intravaginal challenge was obtained, the infection was not prevented (Bourne et al, 1996 (a) and (b)). However, in the present study we obtained 100% protection in the presence of very low levels of antibodies (none detectable in the vaginal washing). Furthermore, in contrast to what was observed after intramuscular immunisation, no virus was recovered in vaginal washes after challenge.

Recently, the question of which type of immunity is involved in protection after a mucosal challenge was readdressed (Kuklin et al, 1997). It is now believed that protection against HSV infection is mediated by T cells and that IFN-γ-producing cells may play a major role.

In previous studies it was shown that high levels of specific secretory IgA were not enough to protect mice against an intravaginal infection with high or even low doses of HSV (Kuklin et al, 1997). The conclusion that antibodies at the site of mucosal infection was usually inadequate to prevent invasion came from experiments in which mice immunised intranasally with recombinant vaccinia expressing HSV glycoproteins were challenged vaginally with HSV. Despite high titers of both IgA and IgG vaginal antibodies against the immunising glycoprotein, following viral challenge infection occurred and virus was recovered from vaginal washes. Furthermore, the infection was confirmed because Ab response against other glycoproteins were induced, and in addition challenged animals developed secondary Ab responses to the immunising glycoprotein.

This pattern of events was evident even in some immune animals challenged with a minimal dose of virus (Kuklin et al, 1998).

Herein, we present data that strongly support the idea that cellular immunity is responsible for the clearance of the virus. Our results show that, after intravaginal challenge, mice immunised with salmonellae carrying a plasmid comprising the glycoprotein D gene (pCIgD) did not develop a secondary antibody response against the immunising glycoprotein. Furthermore, in contrast to what we observed after intra-muscular immunisation with naked plasmid-DNA, immunisation with salmonellae harboring the pCIgD vector results in the absence of virus in the vaginal tract after the challenge, i.e. complete viral clearance. Cellular immunity can additionally be stimulated using cytokines such as Granulocyte Macrophage Colony Stimulating Factor (GMCSF), Interleukin-12 or other molecules that enhance the cellular immune response. According to the invention, therefore, coadministration of such molecules may assist in securing viral clearance.

Currently, there is no effective prophylactic HSV vaccine and the prevalent idea is that immunity to HSV is seldom if ever adequate to prevent viral invasion. Herein, we provide results indicating that immunisation with salmonealla harboring the glycoprotein D gene induce a strong activation of IFN-γ-secreting cells at mucosal and systemic level, similar to those observed after a primary infection.

Our results open up the possibility of preparing a prophylactic vaccine against HSV. The success of this strategy of immunisation to prevent the infection could be due to the fact that the right immune response is induced in the right places, that is a strong activation of IFN-γ-secreting cells in systemic and mucosal compartments including the genital tract.

Accordingly, the invention provides:

A vaccine against herpes simplex virus (HSV) comprising an invasive but attenuated or non-pathogenic bacterium, which bacterium comprises a coding sequence encoding a HSV antigen in a form that enables said coding sequence to be transferred to a host cell of a human or animal host which the bacterium is capable of invading and to be expressed in said cell to form said antigen without the introduction of an antimicrobial agent to lyse the bacterium.

The invention also provides:

A bacterium as just defined (a bacterium of the invention).

The invention also provides:

A bacterium of the invention for use in a method of treatment of the human or animal body.

The invention also provides:

Use of a bacterium of the invention in the manufacture of a medicament for the treatment or prevention of an HSV-mediated human or animal disease.

The invention also provides:

A method of treating or preventing HSV-mediated disease in a human or animal host comprising administering to said subject an HSV vaccine comprising an invasive but attenuated or non-pathogenic bacterium comprising a coding sequence encoding a herpes simplex virus (HSV) antigen in a form that enables said coding sequence to be transferred to a host cell of a mammalian host animal which the bacterium is capable of invading and to be expressed in said cell to form said antigen, in an amount effective to secure vaccination by means of transfer of said coding sequence to said host cell and expression in said host cell without the introduction of an antimicrobial agent to lyse the bacterium.

The invention also provides:

A pharmaceutical composition for vaccination against HSV-mediated disease comprising a bacterium of the invention.

DETAILED DESCRIPTION OF THE INVENTION

Bacteria

Figure 1A:
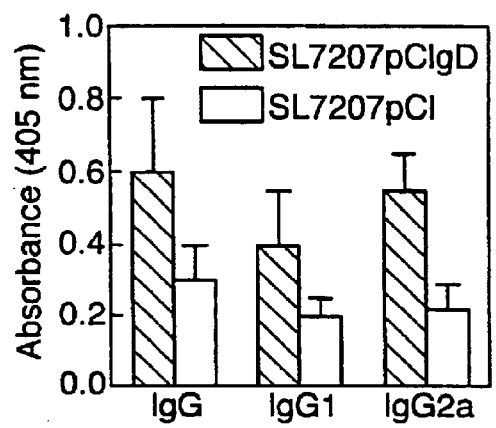
FIG. 1: A) Subclass distribution of specific antibody response in serum. Mice were immunised with salmonella harboring pCIgD or pCI plasmid. Fifteen days after the last dose the levels of antibodies against epitopes 8–23 was determined by ELISA at a dilution 1/100. B) Development of DTH reation in SL7207pCIgD or SL7207pCI immunised mice. Each group of six mice was immunised as was described in methods. For the DTH assay, each mouse was injected with either $10^8$ UV inactivated HSV (titrated before inactivation) in the right ear pinna or BHK extract in the left ear pinna. $*p<0.01$. C) Expression of IL-2R by CD4+ spleen cells after in vitro stimulation with UV inactivated HSV (left panel) or with mock antigen (right panel). A gate on CD4+ T cell was performed and the histograms for IL-2R expression were displayed. Values represent the mean±SD from five animals per group. For the statistical analysis the Mann Whitney U test was used.

The bacteria of the invention are either attenuated or non-pathogenic. This is to prevent the bacteria causing disease in the subject being treated. One alternative is to use bacteria which do not naturally have pathogenic characteristics. Another alternative is to use attenuated bacteria, i.e. bacteria whose pathogenic characteristics have been eliminated or reduced to a clinically acceptable level. Herein, the term "attenuated" covers any bacterium whose undesirable characteristics have been reduced to an acceptable level by any means. Bacteria may thus be attenuated by any suitable means known in the art.

Attenuated Bacteria

Typically, attenuation is effected by introducing one or more attenuating mutations. Known attenuating techniques and mutations may be used, or new ones may be devised by those of skill in the art in the context of the invention.

Attenuating mutations can be introduced into bacterial pathogens using non-specific mutagenesis either chemically, using agents such as N-methyl-N'-nitro-N-nitrosoguanidine, or using recombinant DNA techniques; classical genetic techniques, such as Tn10 mutagenesis, P22-mediated transduction, λ phage mediated crossover, and conjugational transfer, or site-directed mutagenesis using recombinant DNA techniques. Recombinant DNA techniques are preferred. Examples of such attenuating mutations include:

(i) auxotrophic mutations, such as aro (Hoiseth et al, *Nature*, 291: 238–239 (1981), gua (McFarland et al, *Microbiol. Path.*, 3:129–141 (1987), nad (Park et al, *J. Bact.*, 170:3725–3730 (1988), thy (Nnalue et al, *Infect. Immun.* 55:955–962 (1987), and asd (Curtiss, supra) mutations;

(ii) mutations that inactivate global regulatory functions, such as cya (Curtiss et al, *Infect. Immun.*, 55:3035–3043 (1987), crp (Curtiss et al (1987), supra), phoP/phoQ (Groisman et al, *Proc. Natl. Acad. Sci.*, USA, 86:7077–7081 (1989); and Miller et al, *Proc. Natl. Acad. Sci.*, USA, 86:5054–5058 (1989), phoP$^c$ (Miller et al, *J. Bact.*, 172: 2485–2490 (1990)) or ompR (Dorman et al, *Infect. Immun.*, 57: 2136–2140 (1989)) mutations;

(iii) mutations that modify the stress response, such as recA (Buchmeier et al, *Mol. Micro.*, 7:933–936 (1993)), btrA (Johnson et al, *Mol. Micro.*, 5:401–407 (191)), htpR (Neidhardt et al, *Biochem. Biophys. Res. Com.*, 100:894–900 (1981)), hsp (Neidhardt et al, *Ann. Rev. Genet.*, 18:295–329 (1984)) and groEL (Buchmeier et al, *Sci.*, 248:730–732 (1990)) mutations;

(iv) mutations in specific virulence factors, such as lsyA (Libby et al, *Proc. Natl. Acad. Sci.*, USA, 91:489–493 (1994)), pag or prg (Miller et al (1990), supra; and Miller et al (1989), supra), iscA or virG (d'Hauteville et al, *Mol. Micro.*, 6:833–841 (1992)), plcA (Mengaud et al, *Mol. Microbiol.*, 5:367–72 (1991); Camilli et al, *J. Exp. Med.*, 173:751–754 (1991)), and act (Brundage et al, *Proc. Natl. Acad. Sci.*, USA, 90:11890–11894 (1993)) mutations;

(v) mutations that affect DNA topology, such as topA (Galan et al, *Infect. Immun.*, 58:1879–1885 (1990)) mutation;

(vi) mutations that block biogenesis of surface polysaccharides, such as rfb, galE (Hone et al, *J. Infect. Dis.*, 156:164–167 (1987)) or via (Popoff et al, *J. Gen. Microbiol.*, 138:297–304 (1992)) mutations;

(vii) mutations that modify suicide systems, such as sacB (Recorbet et al, *App. Environ. Micro.*, 59:1361–1366 (1993); Quandt et al, *Gene*, 127:15–21 (1993)), nuc (Ahrenholtz et al, *App. Environ. Micro.*, 60:3746–3751 (1994)), hok, gef, kil, or phlA (Molin et al, *Ann. Rev. Microbiol.*, 47:139–166 (1993)) mutations;

(viii) mutations that introduce suicide systems, such as lysogens encoded by P22 (Rennell et al, *Virol.*, 143:280–289 (1985)), λ murein transglycosylase (Bienkowska-Szewczyk et al, *Mol. Gen. Genet.*, 184:111–114 (1981)) or S-gene (Reader et al, *Virol.*, 43:623–628 (1971); and (ix) mutations that disrupt or modify the correct cell cycle, such as minB (de Boer et al, *Cell*, 56:641–649 (1989)) mutation.

The attenuating mutations can be either constitutively expressed or under the control of inducible promoters, such as the temperature sensitive heat shock family of promoters (Neidhardt et al, supra), or the anaerobically induced nirB promoter (Harborne et al, *Mol. Micro.*, 6:2805–2813 (1992)), or repressible promoters, such as uapA (Gorfinkiel et al, *J. Biol. Chem.*, 268:23376–23381 (1993)) or gev (Stauffer et al, *J. Bact.*, 176:6159–6164 (1994)).

Invasive Bacteria

In addition to being attenuated or non-pathogenic, the bacteria of the invention are invasive. An invasive bacterium is one which is capable of entering the subject's body in such a way that it is able to deliver the coding sequence encoding the HSV antigen of the invention in a manner which allows expression of that sequence by cells of the host. Invasive bacteria include bacteria that are naturally capable of entering the cytoplasm or nucleus of animal cells and also bacteria that are not naturally capable of this but that have been altered to become so capable. Thus, any invasive bacterium can be used. The bacterium which is used may be chosen to complement the host to be treated. For example, where treatment of humans is concerned, a bacterium which naturally infects humans may be used.

Preferred naturally occurring invasive bacteria include Samonella spp., Shigella spp., Listeria spp., Rickettsia spp. and enteroinvasive *Escherichia coli*. Salmonella is preferred.

Amongst these species, any suitable strain of bacterium may be used.

One example of a suitable Salmonella strain (see the examples) is the auxotrophic *S. typhimurium* AroA⁺ strain SL7207. Other examples of Salmonella include *Salmonella typhi* (ATCC No. 7251) and *S. typhimurium* (ATCC No. 13311). Attenuated Salmonella strains are preferably used in the present invention and include *S. typhi* aroAaroD (Hone et al, *Vacc.*, 9:810–816 (1991) and *S. typhimurium* aroA mutant (Mastroeni et al, *Micro. Pathol.*, 13:477–491 (1992)).

Alternatively, new attenuated strains can be constructed by introducing an attenuating mutation either singularly or in conjunction with one or more additional attenuating mutations. The same applies to the construction of new attenuated strains of other bacteria.

Examples of Shigella strains include *Shigella flexneri* 2a (ATCC No. 29903), *Shigella sonnei* (ATCC No. 29930), and *Shigella disenteriae* (ATCC No. 13313). An attenuated Shigella strain, such as *Shigella flexneri* 2a 2457T ΔaroAΔvirG mutant CVD 1203 (Noriega et al, supra), *Shigella flexneri* M90T ΔicsA mutant (Goldberg et al, *Infect. Immun.*, 62:5664–5668 (1994)), *Shigella flexneri* Y SFL114 aroD mutant (Karnell et al, *Vacc.*, 10:167–174 (1992)), and *Shigella flexneri* ΔaroAΔaroD mutant (Verma et al, *Vacc.*, 9:6–9 (1991)) is preferably employed.

Examples of Listeria strains which can be employed in the present invention include *Listeria monocytogenes* (ATCC No. 15313). Attenuated Listeria strains include monocytogenes ΔactA mutant (Brundage et al, supra) or *L. monocytogenes* ΔplcA (Camilli et al, *J. Exp. Med.*, 173:751–754 (1991).

Examples of Rickettsia strains include *Ricketsia rickettsiae* (ATCC Nos. VR149 and VR891), *Ricketsia prowaseckii* (ATCC No. VR233), *Ricketsia tsutsugamuchi* (ATCC Nos. VR312, VR150 and VR609), *Ricketsia mooseri* (ATCC No. VR144), *Ricketsia sibirica* (ATCC No. VR151), and *Rochalimaea quitana* (ATCC No. VR358).

Examples of enteroinvasive Escherichia strains include *Escherichia coli* strains 4608-58, 1184-68, 53638-C-17, 13-80, and 6-81 (Sansonetti et al, *Ann. Microbiol.* (Inst. Pasteur). 132A:351–355 (1982)).

Examples of bacteria which can be genetically engineered to be invasive include Yersinia spp., Escherichia spp., Klebsiella spp., Bordetella spp., Neisseria spp., Aeromonas spp, Franciesella spp., Corynebacterium spp., Citrobacter spp., Chlamydia spp., Hemophilus spp., Brucella spp., Mycobacterium spp., Legionella spp., Rhodococcus spp., Pseudomonas spp., Helicobacter spp., Salmonella spp., Vibrio spp., Bacillus spp. and Erysipelothrix spp. These organisms can be engineered to mimic the invasive properties of bacteria such as Shigella spp., Listeria spp., Rickettsia spp., or enteroinvasive *E. coli* spp. by inserting genes that enable them to access the cytoplasm of an animal cell. This may be done by any suitable technique known in the art.

Examples of such genes include the genes incoding the invasive proteins of *Salmonella Shigella*, other invasive bacteria, e.g. as mentioned herein, hemolysin or the invasion plasmid of Escherichia, or listeriolysin O of Listeria, as such techniques are known to result in strains that are capable of entering the cytoplasm of infected animal cells (Formal et al, *Infect. Immun.*, 46:465 (1984); Bielecke et al, *Nature*, 345:175–176 (1990); Small et al, In: *Microbiology*—1986, pages 121–124, Levine et al, Eds., American Society for Microbiology, Washington, D.C. (1986); and Zychlinksy et al, *Molec. Micro.*, 11:619–627 (1994)). Any gene or combination of genes, from one or more sources, that mediates entry into the cytoplasm of animal cells will suffice. Thus, such genes are not limited to bacterial genes, and include viral genes, such as influenza virus hemagglutinin HA-2 which promotes endosmolysis (Plank et al, *J. Biol. Chem.*, 269:12918–12924(1994)).

Invasive genes can be introduced into the target strain using chromosome or plasmid mobilisation (Miller, *A Short Course in Bacterial Genetics*, Cold Spring Harbor Laboratory Press, Cold Spring Harbor, N.Y. (1992); Bothwell et al, supra; and Ausubel et al, supra), bacteriophage-mediated transduction (de Boer, supra; Miller, supra; and Ausubel et al, supra), or chemical (Bothwell et al, supra; Ausubel et al, supra, Felgner et al, supra; and Farhood, supra), electroporation (Bothwell et al, supra; Ausubel et al, supra; and Sambrook, *Molecular Cloning: A Laboratory Manual*, Cold Spring Harbor Laboratory Press, Cold Spring Habor, N.Y.) and physical transformation techniques (Johnston et al, supra; and Bothwell, supra). The genes can be incorporated on bacteriophage (de Boer et al, *Cell*, 56:641–649 (1989)), plasmids vectors (Curtiss et al, supra) or spliced into the chromosome (Hone et al, supra) of the target strain.

Examples of Yersinia strains include *Y. enterocolitica* (ATCC No. 9610) or *Y. pestis* (ATCC No. 19428). Attenuated Yersinia strains include *Y. enterocolitica* Ye03-R2 (al-Hendy et al, *Infect. Immun.*, 60:870–875 (1992) or *Y. enterocolitica* aroA (O'Gaora et al, *Micro. Path.*, 9:105–116 (1990)).

Examples of Escherichia strains include *E. coli* H10407 (Elinghorst et al, *Infect. Immum.*, 60:2409–2417 (1992), and *E. coli* EFC4, CFT325 and CPZ005 (Donnenberg et al, *J. Infect. Dis.*, 169:831–838 (1994)). Attenuated Escherichia strains include the attenuated turkey pathogen *E. coli* 02 carAB mutant (Kwaga et al, *Infect. Immun.*, 62:3766–3772 (1994)).

Examples of Klebsiella strains include *K. pneumoniae* (ATCC No. 13884).

Examples of Bordetella strains include *B. bronchiseptica* (ATCC No. 19395).

Examples of Neisseria strains include *N. meningitidis* (ATCC No. 13077) and *N. gonorrhoeae* (ATCC No. 19424). Attenuated Neisseria strains include *N. gonorrhoeae* MS11 aro mutant (Chamberlain et al, *Micro. Path.*, 15:51–63 (1993)).

Examples of Aeromonas strains include *A. eucrenophila* (ATCC No. 23309).

Examples of Franiesella strains include *F. tularensis* (ATCC No. 15482).

Examples of Corynebacterium strains include *C. pseudotuberculosis* (ATCC No. 19410).

Examples of Citrobacter stains include *C. freundii* (ATCC No. 8090).

Examples of Chlamydia strains include *C. pneumoniae* (ATCC No. VR1310).

Examples of Hemophilus strains include *H. sornnus* (ATCC No. 43625).

Examples of Brucella strains include *B. abortus* (ATCC No. 23448).

Examples of Mycobacterium strains include *M. intracellulare* (ATCC No. 13950) and *M. tuberculosis* (ATCC No. 27294).

Examples of Legionella strains include *L. pneumophila* (ATCC No. 33156). Attenuated Legionella strains include *L. pneumophila* mip mutant (Ott, *FEMS Micro. Rev.*, 14:161–176(1994).

Examples of Rhodococcus strains include *R. equi*.

Examples of Pseudomonas strains include *P. aeruginosa* (ATCC No. 23267).

Examples of Helicobacter strains include *H. mustelae* (ATCC No. 43772).

Examples of Vibrio strains include *Vibrio cholerae* (ATCC No. 14035) and *Vibrio cincinnatiensis* (ATCC No. 35912). Attenuated strains include *V. cholerae* RSI virulence mutant (Taylor et al, *J. Infect. Dis.*, 170:1518–1523 (1994)) and *V. cholerae* ctxA, ace, zot, cep mutant (Waldor et al, *J. Infect. Dis.*, 170:278–283 (1994)).

Examples of Bacillus strains include *Bacillus subtilis* (ATCC No. 6051). Attenuated strains include *B. anthracis* mutant pX01 (Welkos et al, *Micro. Pathol.*, 14:381–388 (1993)) and attenuated BCG strains (Stover et al, *Nat.*, 351:456–460 (1991)).

Examples of Erysipelothrix strains include *Erysipelothrix rhusiopathiae* (ATCC No. 19414) and *Erysipelothrix tonsillarum* (ATCC No. 43339). Attenuated strains include *E. rhusiopathiae* Kg-1a and Kg-2 (Watarai et al, *J. Vet. Med. Sci.*, 55:595–600 (1993) and *E. rhusiopathiae* ORVAC mutant (Markowska-Daniel et al, *Int. J. Med. Microb. Virol. Parisit. Infect. Dis.*, 277:547–553 (1992)).

Antigens

Any HSV antigen may be delivered. Antigens may be derived from any strain of either serotype (HSV-1 or HSV-2) of HSV. Preferred HSV antigens include glycoprotein D, glycoprotein H, glycoprotein B and ICP27. Any suitable antigenic protein may be used, and such antigenic proteins may be structural or non-structural in nature.

According to the invention, vaccination may thus be achieved against any HSV strain. Generally, vaccination against HSV strains that are medically problematical to humans will be most desirable. However, veterinary aspects are also of interest. Thus, vaccination of animals against HSV strains that infect them is also an aspect of the invention. Vaccination of mammals is preferred in this context. Livestock animals, including bovine, ovine, suine and equine livestock such as cows, sheep, goats, pigs and horses is desirable, as is vaccination of companion animals such as cats and dogs. Vaccination of avian hosts, i.e. birds, is also preferred. Poultry species of birds, e.g. chickens, turkeys, ducks, geese and pheasants are especially preferred for vaccination in this context.

Typically, a full-length HSV antigen having the sequence of the naturally occurring antigen will be used. However, modified antigens can also be used. For example, fragments of naturally occurring antigens can be used, as can mutants having a slightly different amino acid sequence. Such modified antigens can be prepared by any means known in the art, typically recombinant means, for example site-directed mutagenesis. Modified, e.g. mutated and truncated antigens, are considered to be HSV antigens in the context of the invention. Such modified antigens can be used if they retain a sufficient degree of antigenicity, e.g. if they have a degree of antigenicity equivalent to the full-length antigen. Preferably, if a modified antigen has a lower degree of antigenicity than the naturally occurring antigen, it will still have a high enough degree to ensure that a prophylactic effect sufficient to ensure complete viral clearance from the subject's mucosae is conferred. However, the invention also encompasses the use of modified antigens that achieve lesser degrees of clearance.

In this context, a vaccine of the invention may secure any statistically significant degree of viral clearance, e.g. from the genital tract, for example up to 99%, up to 95%, up to 90%, up to 80%, up to 70%, up to 50%, up to 20% or up to 10%. As discussed in more detail below, this may be measured by reference to viral titers in vaccinated and non-vaccinated subjects or titers before and after vaccination in a single subject in some cases. Where a lesser degree of clearance is achieved, it may be desirable to use an alternative anti-HSV treatment in combination with the treatment of the invention.

Expression of Antigens

According to the invenion, HSV antigens are expressed, by any suitable mechanism, in eukaryotic cells of the host, which is the first step in the route to vaccination against HSV-mediated disease. Coding sequences encoding HSV antigens are delivered to the cells by means of an attenuated or non-pathogenic but invasive bacterium as discussed herein. Within the bacterium, the coding sequence is typically operably linked to regulatory sequences capable of securing the expression in the target host cell. In principle, however, the coding sequence can be integrated into the host cell genome such that expression is driven by host regulatory sequences.

Thus, the coding sequence is typically operably linked to a promoter capable of driving expression in the host cell. Typically, this would be a eukaryotic promoter, though it could be any promoter capable of securing expression. For example, instead of a promoter derived from a eukaryotic organism, it could be a promoter derived from a virus which infects eukaryotic cells.

Any promoter capable of securing expression in the host cell may be used. Suitable promoters include the SV40, CMV and retroviral LTR promoters, as well as HEF 1α and PDGF promoters.

In general, the coding sequence will be comprised within an expression construct. Such constructs typically comprise: a promoter (see above) capable of directing the expression of the coding sequence of the invention, and optionally a regulator of the promoter, a translational start codon, and, operably linked to the promoter, a coding sequence according to the invention. Preferably, these components are arranged in a 5'-3' orientaion.

The construct may also comprise any other suitable components. For example, the construct may comprise a nucleic acid encoding a signal sequence, so positioned in such a position relative to the coding sequence such that, when it is translated, it is capable of directing the expressed protein to a given cell type or cell compartment. Any such signal sequence will typically be positioned immediately 3' or immediately 5' to the coding sequence, such that the signal sequence and coding sequence are translated as a single fusion protein, with the signal sequence at the C- or N-terminus.

The construct may also comprise an enhancer which enhances the degree of expression provided by the promoter. Any enhancer which enhances the expression provided by the selected promoter may be used.

Optionally, the construct may comprise a transcriptional terminator 3' to the coding sequence. Any suitable terminator may be used.

Optionally, the construct may comprise a polyadenylation signal operably linked 3' to the coding sequence.

Optionally, the construct may comprise one or more selectable marker genes, e.g. antibiotic resistance genes, to allow selection of transformed cells in culture. For example, cells may selected for antibiotic resistance.

Optionally, the construct may comprise one or more introns, or other non-coding sequences, for example 3' or 5' to the coding sequence. In the context of the invention, these may be useful in checking that expression takes place in the eukaryotic cells of the host, not the bacterial ones of the delivery system.

Additional genetic elements may be included. Such elements include mammalian artificial chromosome elements or elements from the autonomous replicating circular minichromosomes, such as found in DiFi colorectal cancer cells, to allow stable non-integrated retention of the expression cassette (Huxley et al, *Bio/Technology*, 12:586–590 (1994); and Untawale et al, *Canc. Res.*, 53:1630–1636 (1993)), integrase to direct integration of the expression cassette into the recipient cell's chromosome (Bushman, *Proc. Natl. Acad. Sci.*, USA, 91:9233–9237 (1994), the inverted repeats from adeno-associated virus to promote non-homologous integration into the recipient cells chromosome (Goodman et al, *Blood*, 84:1492–1500 (1994), recA or a restriction enzyme to promote homologous recombination (WO9322443 (1993); and WO9323534-A (1993)) or elements that direct nuclear targeting of the eukaryotic expression cassette (Hodgson, supra; and Lewin, supra).

Typically, the expression construct will be comprised within a vector, preferably for example a plasmid vector.

According to the invention, it is not necessary to introduce an antimicrobial agent to lyse the bacterium. This is a distinction between the methods of the present invention and those of WO 98/44131 (Walter Reed, supra) where the antigen-encoding DNA cannot be released except by lysing the bacteria with an antimicrobial agent introduced for that purpose.

HSV-mediated Disease

Any HSV-mediated disease can be treated according to the invention. HSV-1-mediated diseases may be treated, as may HSV-2-mediated diseases. In particular, dental herpes, oral/facial infections (e.g. gingivostomatitis, labialis, pharyngitis), cutaneous infections, (e.g. whitlow, herpes gladatorium), ocular infections, neonatal herpes, herpes encephalitis, disseminated infection and erythema multiforme. Treatment of genital herpes is particularly preferred. As discussed herein, both human and animal HSV-mediated disease can be treated and prevented according to the invention.

As discussed above, the present invention is principally concerned with prophylactic vaccines, which is to say vaccines that prevent infection from taking place. Preferably, complete prevention is achieved, as measured by complete clearance of HSV from a subject, typically measured at a mucosal surface of the subject, e.g. the vaginal tract, after challenge with HSV. As a specific test, clearance from the vaginal tract after intravaginal challenge with $5 \times 10^6$ PFU of HSV may be measured by determining viral titers before and after challenge or in vaccinated and non-vaccinated subjects. Preferably, complete clearance is achieved. However, vaccines that achieve a lesser degree of clearance are also within the scope of the invention. A vaccine of the invention may achieve any statistically significant degree of clearance, for example up to 99%, 95%, 90%, 80%, 70%, 50% and 20% clearance. Where lesser degrees of clearance are achieved, it may be desirable to combine vaccination according to the present invention with another type of vaccination or treatment.

In the context of prophylactic vaccines, clearance will typically be measured by comparing the degree of viral clearance in vaccinated and non-vaccinated subjects. This can be measured by comparing viral titers in the two types of subject Viral titers can be measured by any suitable means, e.g. as described in the Examples or by any other known method.

Although the present invention is principally concerned with prophylactic vaccines, the invention can also be applied to the design of therapeutic vaccines as appropriate. Thus, both prophylactic and therapeutic vaccines are provided.

In the context of therapeutic vaccines, efficacy will typically be measured in a similar manner to that described above for prophylactic vaccines, i.e. by measuring the degree of viral clearance achieved by measuring viral titers in subjects. However, the comparison will typically be between the viral titers in a single subject at different times, i.e. before and after administration of the vaccine.

As discussed above, the vaccines of the invention will typically act by eliciting cellular immunity, specifically cellular mucosal immunity. Such immunity may arise at any or all the body's mucosal surfaces, most preferably the genital mucosae.

Pharmaceutical Formulations, Routes of Delivery and Dosages

Typically, a vaccine of the invention will contain bacteria of the invention in combination with a pharmaceutically acceptable carrier or diluent.

Examples of diluents include a phosphate buffered saline, buffer for buffering against gastric acid in the stomach, such as citrate buffer containing sucrose, bicarbonate buffer alone (Levine et al, *J. Clin. Invest.*, 79:888–902 (1987); and Black et al, *J. Infect. Dis.*, 155:1260–1265 (1987), or bicarbonate buffer containing ascorbic acid, lactose, and optionally aspartame (Levine et al, *Lancet*, II:467–470 (1988)). Examples of carriers include proteins, e.g., as found in skim milk, sugars, e.g. sucrose, or polyvinylpyrrolidone. Typically these carriers would be used at a concentration of about 0.1–90% (w/v) but preferably at a range of 1–10% (w/v).

Vaccines of the invention may be administered by any suitable route and will be formulated accordingly. Preferably, delivery will be to a mucosal surface, most preferably a genital mucosal (e.g. vaginal) surface. Another preferred route of delivery is oral delivery. Alternatively, intrarectal or intranasal delivery may be used as may delivery to the respiratory tract, in which case the vaccine may be formulated as respiratory spray.

The amount of the live invasive bacteria of the present invention to be administered will vary depending on the species of the subject, as well as the disease or condition that is being treated. Generally, the dosage employed will be about $10^3$ to $10^{11}$ viable organisms, preferably about $10^5$ to $10^9$ viable organisms, e.g. about $10^6$, $10^7$ or $10^8$. For Samonella, doses will typically be in the range of $10^5$ to $10^{11}$ viable organisms. Lower doses may be possible with other microorganisms that are naturally invasive or are engineered to be invasive.

Combination Treatments

This efficacy of a vaccine of the invention may be enhanced by the use of stimulatory agents capable of stimulating cellular immunity, preferably cellular mucosal immunity. These may be co-administered with the vaccine, for example, as part of the vaccine (by the same means of delivery), or at the same time as the vaccine but by a different means of delivery. Alternatively, the stimulatory agent may be administered at a different time, but close enough in time to the administration of the vaccine to have a combined prophylactic or therapeutic effect. Thus, the vaccine and the stimulatory agent may be administered simultaneously, sequentially or separately.

Any agent capable of stimulatory cellular immunity may be used. Cytokines having this property are one option. GMCSF (granulocyte macrophage colony stimulating factor) is preferred, as is Interleukin-12 (IL-12).

Interleukin-14 (IL-14) can also be used, to stimulate other types of immune response, in combination with the treatments of the invention.

Additionally, treatments of the invention may be combined with any other type of treatment for HSV infection, e.g. other prophylactic or therapeutic treatments.

Vaccination Against Viral Diseases in General

Although the principal object of this invention is to combat HSV-mediated disease, the teachings of the invention can also be applied to combat infection by other viruses that infect the mucosae of human and/or animal hosts. All of the foregoing discussion relating to HSV vaccines applies equally to vaccines according to this aspect of the invention.

According to this aspect of the invention, any viral infection that may be treated or prevented by stimulating cellular mucosal immunity by the methods described herein may be combatted by therapeutic or prophylactic vaccination. In this context, some preferred viral infections that may be combatted are, in addition to HSV as described above, infections by Human Immunodeficiency virus (HIV). Hepatitis C virus (HCV), Hepatitis B virus (HBV), Hepatitis A virus (HAV) and Human Papilloma virus (HPV).

Accordingly, this aspect of the invention provides:

A vaccine against a virus which infects the mucosae of a human or animal host, which vaccine stimulates cellular mucosal immunity and comprises a bacterium which is invasive but attenuated or non-pathogenic in respect of said human or animal host and comprises a coding sequence encoding an antigen from said virus in a form that enables said coding sequence to be transferred to a host cell of said human or animal host and to be expressed in said cell to form said antigen.

This aspect of the invenion also provides:

Use of a bacterium of this aspect of the invention, in the manufacture of a vaccine for the treatment or prevention of a viral infection of the mucosae of a human or animal host by stimulating cellular mucosal immunity against the virus.

This aspect of the invenion also provides:

A method of treating or preventing a viral infection of the mucosae a human or animal host by stimulating cellular mucosal immunity against said virus, said method comprising administering to said host an effective amount of a vaccine comprising an invasive but attenuated or non-pathogenic bacterium comprising a coding sequence encoding an antigen from said virus in a form that enables said coding sequence to be transferred to a host cell of a human or animal host which the bacterium is capable of invading and to be expressed in said cell to form said antigen.

This aspect of the invenion also provides:

A pharmaceutical composition for vaccination against a viral infection of the mucosae a human or animal host by stimulating cellular mucosal immunity against said virus which composition comprises a vaccine of this aspect of the invention.

The following Examples illustrate the invention.

EXAMPLES

Methods

Mice

Female BALB/c mice, 6 to 8 weeks of age, were purchased from Harlan (Italy) and maintained at the International Centre of Genetic Engineering and Biotechnology under standard conditions according to Institutional Guidelines.

Viruses

Herpes simplex virus type 2 was grown in BHK cells and was stored in aliquots at −80° C. until used. Titers were measured in Vero cells and expressed as PFU per milliliter.

Media and Reagent

Cells were cultured in RPMI 10% fetal bovine serum (Seromed, Germany). Solid and liquid Luria Bertani medium (LB) was used to grow *E. coli* and *S. typhimurium* strains. Media were supplemented, where required, with 100 μg/ml amplicillin.

Bacterial Strains and Plasmids

The auxotrophic S. AroA strain SL7207 (S. 2337-65 derivative hisG46, DEL407 [aroA::Tn10{Tc-s}]) was kindly provided by B. A. D. Stocker (Stanford University, School of Medicine, Stanford, Calif.). The *E. coli* DH5α was used as host during the cloning experiments and to propagate plasmids. Bacterial strains were routinely grown at 37° C. in LB broth or agar, supplemented with 100 μg/ml ampicillin when required. The eukaryotic expression vector pCI (Promega) was used for cloning the glycoprotein D (gD) of the herpes simplex virus and the green fluorescent protein.

Recombinant DNA Techniques

DNA preparation, genetic manipulations, PCR, and transformation of bacteria were carried out according to standard protocols (Sambrook et al, 1989).

Cloning of gD and GFP into the Eukaryotic Expression Vector pCI

HSV-2 MS strain (ATCC No. VR-540) DNA used as template for polymerase chain reactions (PCR), was prepared from nucleocapsids isolated from BHK cells. For the construction of the eukaryotic expression vector pCIgD a 1.2 kb fragment encoding the gD precursor gene was amplified by PCR using the following primers: forward, GTTCG-GTCATAAACTGCATTGCGAACCACTAGTCG (SEQ ID No. 1); reverse, CCTAGTTTCCCTCCTTCTAGACTC-CCTTTATGCGG (SEQ ID No. 2). The PCR product was cloned in the EcoRI-XCba site of the eukaryotic expression vector pCI and completely sequenced. The GFP was amplified by PCR using as template the CMV2 tracer plasmid (Invitrogen) and then subcloned in the EcoRI-Xba site of the expression vector pCI (pCIGFP). Intron 1 of the human alpha globin gene (117 bp) was introduced into the GFP by PCR-directed mutagenesis at the position 283. The PCR product was cloned as was described above for the GFP (pCIGFPint).

In vitro Evaluation

Plasmids pCIgD, pCIGFP and pCIGFPint were transfected in COS cells using lipofectin (Boehringer) according to manufacturer's instructions. The expression of the GFP was analysed by flow cytometry (Becton Dickinson). The expression of the glycoprotein D was analysed by immunobloting. Briefly, after 48 hr cell lysates were resolved by electrophoresis and then transferred to nitrocellulose membranes. Immunoblots were processed with an anti gD monoclonal antibody (ViroStat) and developed with an enhanced chemiluminescence detection kit (Amersham).

Immunisation and Challenge

Bacteria were grown overnight until they reached stationary phase. They were harvested by centrifugation and resuspended in PBS with 5% sodium bicarbonate. Mice received three groups of doses at 15 days intervals by feeding them with the bacterial suspension using a flexible cannula. Each group of doses consisted in three doses at 2-days intervals of $5-10 \times 10^7$ recombinant *S. typhimurium* AroA strain harboring one of the plasmids described. As control was used the bacterial transformed with the vector pCI alone. For protection studies, 15 days after the last dose of salmonellae, immunised mice were challenged by intravaginal instillation of HSV-2 MS strain. In order to synchronise the estrus cycle, the immunised mice were injected subcutaneously with Depo-Provera (DP) (Upjohn Co., Kalamazoo, Mich.) at a concentration of 3 mg per mouse in 100 μl of distilled water (Parr et al, 1994). Five days after the administration of DP, the animals were anesthesiated with Avertin and the vaginal cavity was washed with PBS previously of the instillation of $5 \times 10^6$ PFU of HSV in 20 μl. The mice were examined daily for vaginal inflammation, neurologic illness and death. The severity of disease was scored 1 to 5 (0, no symptoms; 1, mild inflammation; 2, moderate swelling; 3, severe inflammation; 4, paralysis and 5, death) (Overall et al, 1975). Vaginal washes were collected at different time points after intravaginal challenge by pipetting 200 μl of PBS in the vaginal cavity. The samples were filtered by 0.45 μm filters and stored at −80° C. until titered.

ELISA of Antibodies

To evaluate the levels of specific total IgG or IgG subclasses in serum and in vaginal washes, standard indirect ELISA was employed. Levels of total IgG, IgG1 and IgG2a were determined using affinity-purified rabbit anti-mouse specific for γ, γ1 or γ2a respectively and as second antibody an affinity purified goat anti rabbit IgG HRPO conjugate (Zymed Lab. Inc. San Francisco, Calif.) was used. As antigen for attachment to the plates the whole gD and two synthetic peptides (aa 8–23, and aa 222–252) corresponding to the main neutralising in vitro epitopes (Cohen et al, 1984; Nicola et al, 1998) were used.

Determination of Cytokines after in vitro Stimulation

Cytokines in the culture supernatants were measured by sandwich ELISA using monoclonal antibody pairs ID11/BVD6-24G2, JES6-1A12/JES6-5H4, and R4-6A2/XMG1.2 (Pharmingen, San Diego, Calif.) for interleukin-4 (IL-4), interleukin-2 (IL-2) and interferon-γ (IFN-γ) determination, respectively.

Cytokine ELISPOT Assay

Fifteen days after the last dose of salmonellae, mice were sacrificed and spleen, Peyer patches, mesenteric lymph node and ileal lymph node were removed and cultured for 24 hr in presence of inactivated HSV or mock antigen. After this, cells were added to 96 well nitrocellulose bottom plates (Millipore, HA) precoated with anti cytokine antibody. Cells were cultured for 24 hr and removed. After the addition of the second anti-cytokine monoclonal antibody conjugated with biotin, the HRPO conjugated streptavidin was dispensed. The spots were developed with the substrate AEC (Fujihashi et al, 1993).

Determination of CD25 Expression after in vitro Stimulation

Expression of IL-2R responding to Ag stimulation in vitro was determined by FACS analysis. Spleen cells ($1 \times 10^7$/ml) cultured for 96 hs in the presence of 1/20 dilution of UV inactivated HSV or mock antigen, were collected and doubly stained with PE-labelled anti-mouse CD4 and with FITC-labelled monoclonal antibodies: anti-mouse IL-2R (Pharmingen) for 30 min at 4° C. Cells were washed twice with medium and a two-colour immunofluorescence analysis using a FACScalibur (Becton Dickinson) was performed, with gates set by forward angle light and side scatter. Gates were adjusted to include the discrete mononuclear population and exclude dead cells and debris, and $20 \times 10^3$ cells were analysed per sample.

Delayed-type Hypersensitivity

The DTH response to HSV was tested 15 days after the immunisation. The antigens were injected in 20-μl volumes in the right ear pinna, and ear thickness was measured with a micrometer caliper (Oditest, Mitutoyo, japan) 24 hs later.

Test antigens included UV-inactivated HSV-2 with a titer of $10^8$ prior the inactivation, and mock antigen (BHK cell extract) was injected in the left ear pinna as negative control. The ear thickness was measured in a blinded fashion before and 24 hs after the injection. The DHT-reaction was expressed as the increase in ear thickness following war pinna injection over the prechallenged thickness.

Determination of in vivo Gene Transfer

Mice were fed with SL7207 harboring the either pCIGFP, pCIGFPint or pCIgD vectors, following the schedule of administration described above Lamina propria and Peyer patches cell suspensions were prepared as was previously described by Franco et al (1998). GFP-expressing cells in PP, MLN and LP were detected by flow cytometry 5 days after the last dose. The phenotype of the GFP+ cells was determined by double-fluorescence analysis after staining with anti CD3-PE, anti CD19-PE, anti MAC3-PE or anti CD11c-PE in the presence of Fc blocking reagent (Pharmingen). In other experiments one dose $4 \times 10^6$ SL7207 harboring the plasmids mentioned above were administered intraperitoneally to 3 groups of mice. Two days later peritoneal cells were harvested and GFP+ cells were detected by double fluorescence analysis after staining with MAC3-PE or CD19-PE.

Results

Serum and Mucosal Antibody Response

Mice orally transgen immunised using attenuated salmonella (strain SL7207) harboring the pCIgD plasmid, elicited a weak serum antibody immune response. The reactivity of the antibodies was mainly against the epitope 8–23 whereas very low levels against the epitope 222–252 were detected. Analysis of the IgG subclass distribution in the immune sera indicated IgG2a as the principal isotype, but also IgG1 was evident (FIG. 1A). A very weak serum IgA antibody response was also observed with a pattern of reactivity similar to that described for IgG. Furthermore, no antibody reactivity was observed in the vaginal washes when whole gD or peptides were attached to the plates.

Pattern of Cellular Mediated Immune Response

Figure 1B:
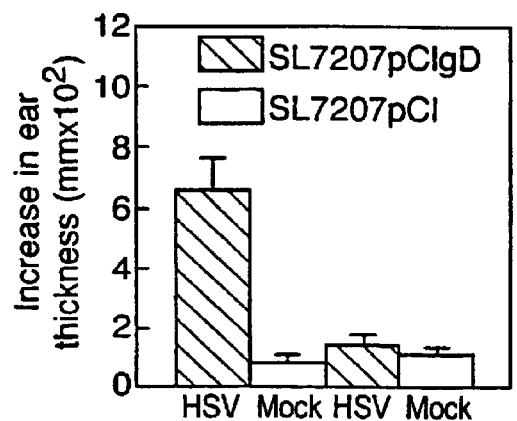
Figure 1C:
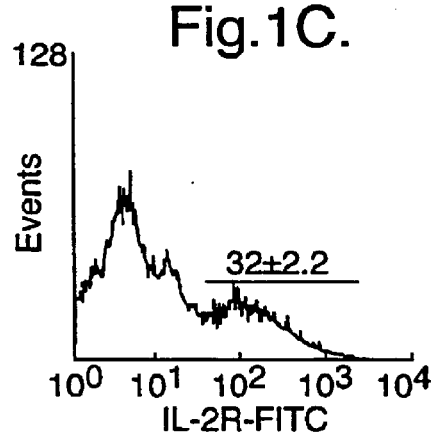
Figure 1D:
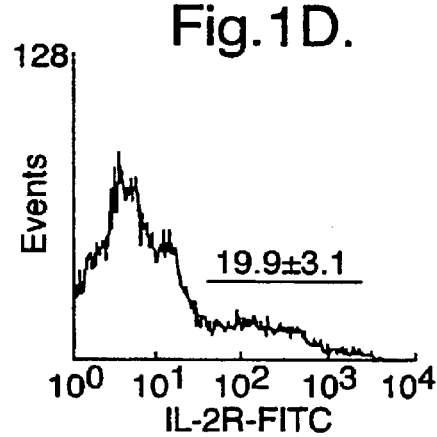
Figure 2A:
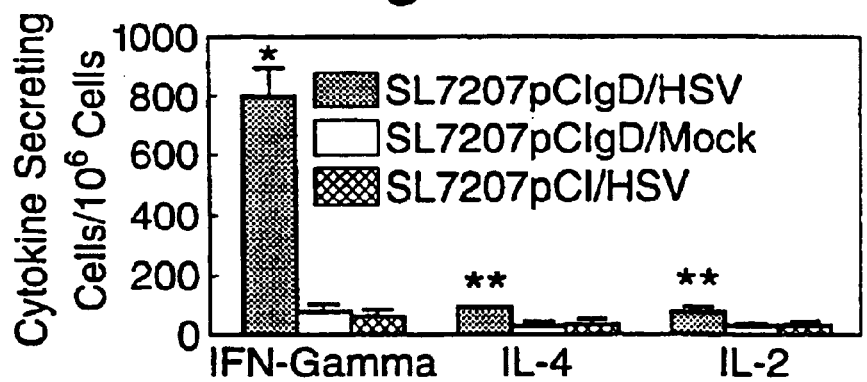
FIG. 2: Mice were immunised with salmonella. Fifteen days after the last immunisation spleen, Peyer patches (PP) and ileal lymph node (ILN) cell suspensions were restimulated in vitro with UV inactivated HSV or mock antigen over a period of 24 hs. Frequencies of cytokine-producing cells in spleen (A), PP (B) and ILN were measured by ELISPOT assay. Pooled data from three experiments (three mice per group in each experiment) are presented. Bars represent the mean±SE. $*p<0.001$, $**p<0.05$.
Figure 2B:
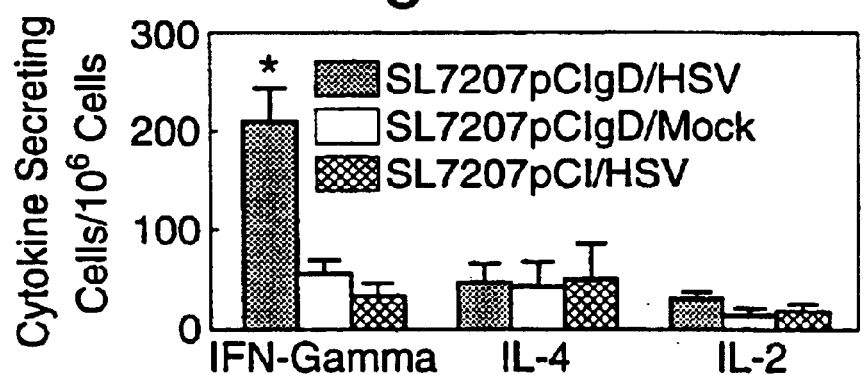
Figure 2C:
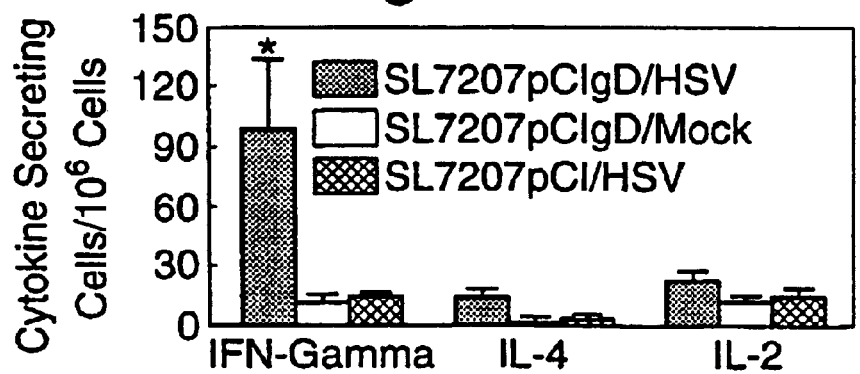
Figure 3:
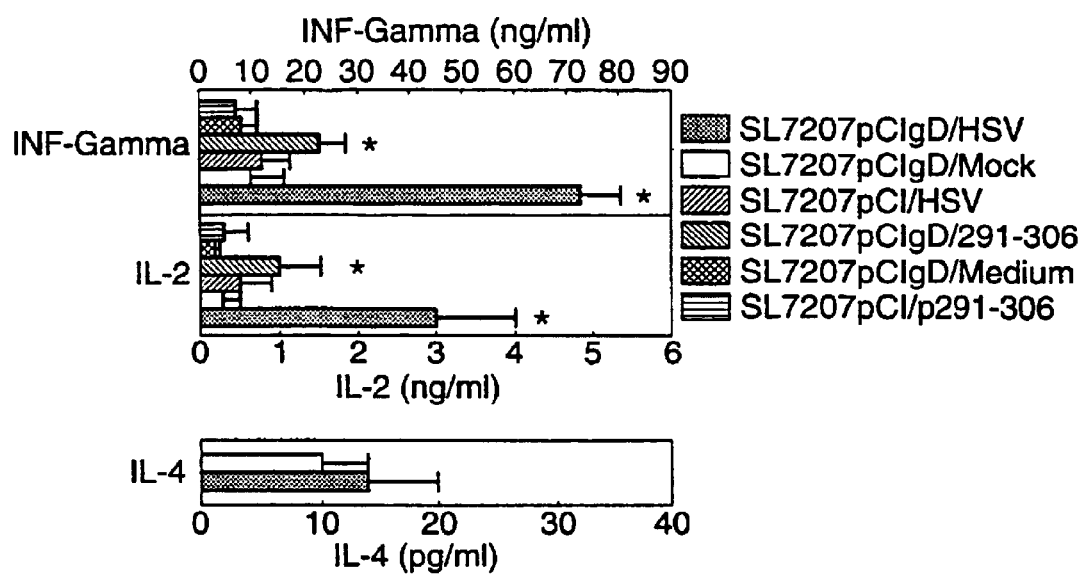
FIG. 3: Profile of cytokines released by HSV, mock or peptide 291–306 stimulated cells from spleen. $10^7$ cells/ml were cultured per quadruplicate in 24 well plates and after 24 and 48 hs of culture, supernatantes were harvested and the level of cytokines was determined by sandwich ELISA. Bars represent the mean±SE. $*p<0.001$.

When spleen cells from mice immunised with SL7207 harboring the pCIgD or the pCI plasmid were cultured in the presence of inactivated HSV or mock antigen, an increase in the expression of IL-2R was observed in the CD4 subset (FIG. 1C). This was taken as an indicator that the transgene immunisation using salmonella results in a specific CD4 activation. To determine whether antigen-specific cell-mediated responses could be detected in vivo, delayed type hypersensitivity (DTH) reaction was measured 15 days after the last dose of salmonella. Significant DTH response was induced in the immunised mice indicating that a Th1 immune response was present (FIG. 1B). The pattern of cell-mediated immune response was directly analysed by enumerating the number of cells in Peyer patches, ileal lymph nodes and spleen, which produce Th1- or Th2-type cytokines upon secondary stimulation in vitro with inactivated HSV or with synthetic peptide (aa 291–306). Mice immunised with SL7207 harboring the pCIgD vector showed a dramatical increase in the IFN-γ secreting cells in spleen, ileal lymph node (ILN) and Peyer patches (PP) (FIG. 2). However, a weak increment in the number of specific IL-2 secreting cells was observed. Surprisingly, we observed an increase of the IL-4 producing cells in the spleen of immunised mice, which could be responsible of the IgG1 immune response observed in serum. When the pattern of cytokines was analysed in the supernatant of cultured lymphocytes after in vitro stimulation, the results were in line with those described above (FIG. 3). However, we did not find significant differences in the levels of IL-4 among the different groups of mice. This may indicate that the analysis at single cell level could be more sensitive than the measure of cytokines in the supernatants.

Resistance Against Viral Invasion after Intravaginal Challenge

Figure 4:
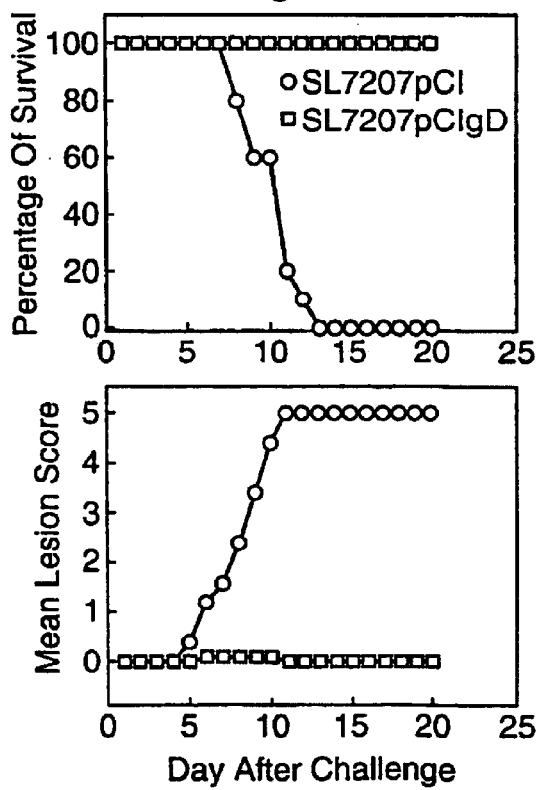
FIG. 4: Protective immune response after oral genetic immunisation. Groups of five mice were immunised as was described in methods with salmonella harboring pCIgD or pCI plasmid. Fifteen days after the last immunisation mice were injected with 3 mg of DP. Five days following the administration of DP mice were challenged intravaginally with $5\times10^6$ PFU of HSV2 MS strain. Numerical scores were assigned to specific disease signs using the following scale: 0, no symptoms; 1, mild inflammation; 2, moderate swelling; 3, severe inflamation; 4, paralysis and 5, death. Daily mean lesion score was calculated by dividing the sum of a group's lesion scores by the number of observations. Graphics represent pooled data from three independent experiments with five mice per group in each experiment.

Fifteen days after the last dose mice were challenged intravaginally with $5 \times 10^6$ PFU. Animals were followed for signs of disease, and vaginal washes were collected for virus titration. All immunised animals were protected and survived challenge, whereas within 13 days post challenge all the controls died (FIG. 4). During the observation period, non-immunised animals showed herpetic lesions. On the other hand, controls showed inflammation, swelling and paralysis prior to death (FIG. 4). One point of the fundamental importance was to determine whether the immune response developed in the immunised mice was enough to prevent viral invasion. If the immunity mounted in immunised animals resulted in total exclusion of the virus, then the virus should be rapidly removed from vaginal tissues and the animals should show no evidence for a systemic secondary immune response to HSV. Indeed no virus could be recovered from vaginal washing of immunised mice (Table 1). Furthermore, when the level of serum antibodies against gD or HSV was determined no secondary immune response was found.

Figure 5:
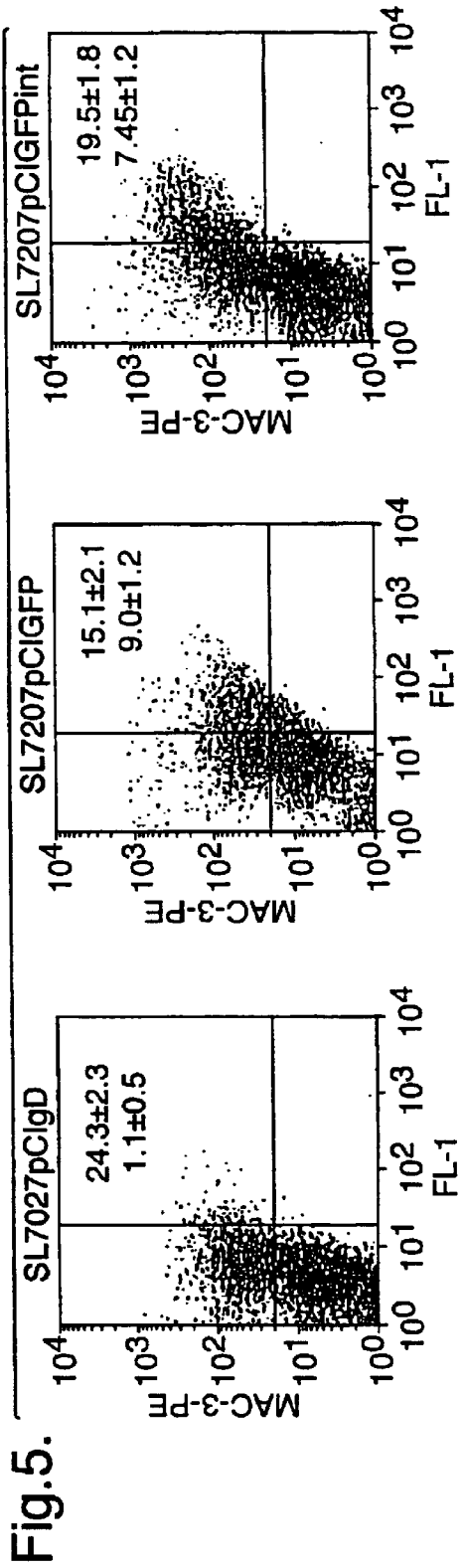
FIG. 5: Expression of GFP in peritoneal macrophages. Three mice per group were inoculated intraperitoneally with $5\times10^6$ salmonellae harboring one of the following plasmids: pCIgD, pCIGFP or pCIGFPint. Two days after the inoculation cells were collected from the peritoneal cavity and the expression of GFP was determined by flow cytometric analysis. Characterisation of the cell subset expressing GFP was done by two colour fluorometric analysis after staining with PE-MAC3 or PE-CD19. No expression of GFP was observed in the CD19+ B cells. The values are the mean±SD from four mice per group.

Characterisation of the in vivo Gene Transfer from the Salmonellae to the Eukaryotic Cells One point to address was to determine whether the immune response observed was against a protein synthesised in vivo by the eukaryotic cells or otherwise it resulted from the expression of the antigen in the bacterial carrier. To assess this, the intron 1 of the human alpha globin gene was introduced in the GFP so that, to obtain a fluorescent protein it needs a splicing process that only can occur in the nucleus. The flow cytometry analysis of the peritoneal macrophages obtained from mice inoculated with one dose of salmonellae harboring the pCIGFP or the pCIGFPint showed similar expression of the GFP (FIG. 5). This result unanswerably confirms that a real gene transfer from bacteria with a de novo synthesis by the host cell have occurred.

Figure 6A:
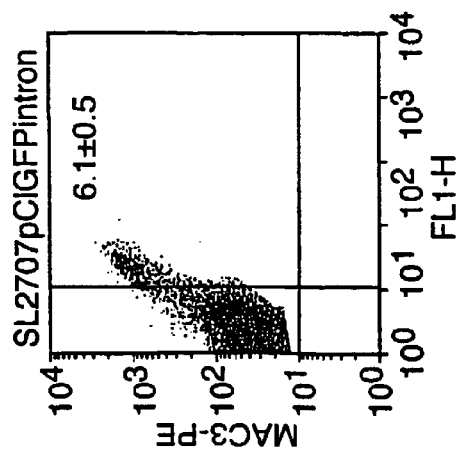
FIG. 6: Characterisation of in vivo *S. typhimurium*-mediated DNA gene transfer. Mice were fed with salmonella harboring one of the following plasmids: pCI, pCIGFP or pCIGFPint. Five days after the last dose the expression of GFP was determined by flow cytometry in Peyer patches (A,B,C), lamina propria of the small intestine (D,E,F) and in the spleen (G,K,I). Cell subsets expressing GFP were identified by two-colour fluorocytometric analysis staining with PE-anti CD19 (B cells). PE-anti CD3 (T cells) or PE-MAC3 (macrophages). Only the macrophage subset expressed GFP. No expression of GFP was found in B or T cells. The values showed represent the mean±SD from four mice).
Figure 6B:
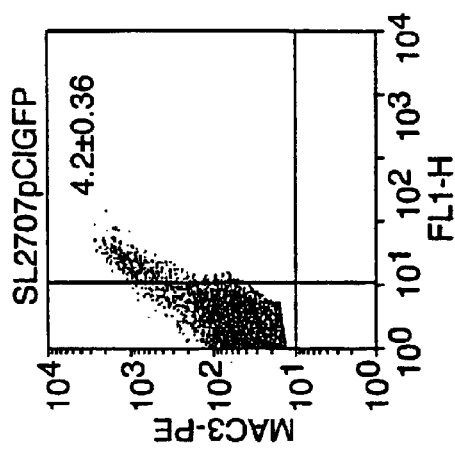
Figure 6C:
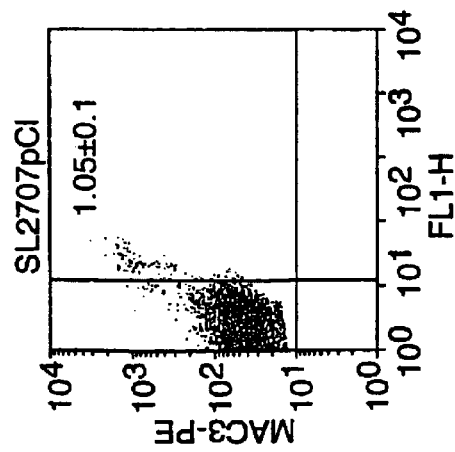

Characterisation of Cells Transfected after the Oral Administration of Salmonellae Harboring the pCIGFPint Vector To determine what kind of cells express the transgene delivered by the orally administered salmonellae carrier and in which organs these cells can be found, mice were fed with the SL7207 strain harboring the pCIGFP, the pCIGFPint or the pCI vectors. The flow cytometric analysis showed the expression of the GFP in cells from PP, spleen and LP of the small intestine. The phenotype of cells expressing GFP was characterised by double fluorescence analysis. Only macrophages and dendritic cells expressed GFP (FIG. 6). No CD19+ or CD3+ lymphocytes were positive for GFP expression.

These data confirm that the use of salmonellae as carrier to delivery DNA-plasmid result in the specific transfection of antigen presenting cells at mucosal and systemic level which could be very important to obtain cellular mediated immune response against virus or intracellular parasites that enter through the mucosal surfaces.

Franco et al, *Cell. Immunol.* 1998; 190:1–11.
Bernstein et al, *Vaccine* 1999; 17:1681–1689.
Chabalgoity et al, *Molecular Microbiology* 1996; 19(4): 791–801
Karem et al, *J. Gen. Virol.* 1997; 87:427–434

TABLE 1

Resistance to HSV challenge in SL7207 pCIgD immunised mice and controls

| Immunisation | No. of mice survived/no. of mice challenged | Log10 of viral titer at day post challenge | | | Serum IgG anti gD titers (aa 8-23) | |
|---|---|---|---|---|---|---|
| | | 1 | 3 | 5 | prechallenge | postchallenge |
| SL7207pCI | 0/15 | 0.9 ± 0.2 (7/8) | 4.5 ± 1.2 (8/8) | 4.8 ± 0.8 (8/8) | ND | ND |
| SL7207pCIgD | 15/15 | 0 (0/7) | 0 (0/7) | 0 (0/7) | 150 ± 80 | 180 ± 40 |

REFERENCES

Bourne et al, *J. Infect. Dis.* 1996 (a) April; 173(4):800–7.

SEQUENCE LISTING

<160> NUMBER OF SEQ ID NOS: 2

<210> SEQ ID NO 1
<211> LENGTH: 35
<212> TYPE: DNA
<213> ORGANISM: Artificial Sequence
<220> FEATURE:
<223> OTHER INFORMATION: PCR primer

<400> SEQUENCE: 1
gttcggtcat aaactgcatt gcgaaccact agtcg        35

<210> SEQ ID NO 2
<211> LENGTH: 35
<212> TYPE: DNA
<213> ORGANISM: Artificial Sequence
<220> FEATURE:
<223> OTHER INFORMATION: PCR primer

<400> SEQUENCE: 2
cctagtttcc ctccttctag actcccttta tgcgg        35

Bourne et al, *Vaccine* 1996 (b) septembre; (136): 1230–1234 (1996).
Kuklin et al, *J. Virol.* 1997 April; 71.(4.4):3138–45.
Kuklin et al, *J. Immuno.* 1998; 160:5998–6003.
Sizemore et al, *Science* 1995; 270:299–302.
Darji et al, *Cell* 1997; 91:765–75.
Paglia et al, *Blood* 1998; 92:3172–6.
Fennelly et al, *J. Immunol.* 1999; 162:1603–10.
Sambrook et al, Molecular cloning: A laboratory manual. Cold Spring Harbor Laboratory Press: Cold Spring Harbor, N.Y., 1989.
Parr et al, *Lab. Invest.* 1994; 70:369–80.
Overall et al, *Infect. Immun.* 1975; 11:476.
Cohen et al, *J. Virol.* 1984 January; 49.(1.1):102–8.
Nicola et al, *J. Virol.* 1998 May; 72.(5.):3595–601.
Fujihashi et al, *Journal of Immunological Methods* 1993; 160:181–9.

What is claimed is:

1. A method of generating an immune response to a herpes simplex virus (HSV) in a human or animal host, said method comprising:

(a) providing an immunogenic compositions; wherein said composition is comprised of an invasive but attenuated or non-pathogenic bacterium selected from the group consisting of *Salmonella, Shigella, Listeria* and *E. coli* bacteria; said bacterium is comprised of a coding sequence encoding a herpes simplex virus (HSV) antigen selected from the group consisting of glycoprotein D, glycoprotein H, glycoprotein B and ICP27; and said coding sequence is comprised within an expression construct and operably linked to one or more regulatory sequences and (b) administering said composition to said host such that said bacterium invades a host cell of said host selected from the group consisting of macrophages and dendritic cells and said expression construct is transferred to said host cell where said regulatory sequences direct expression of said coding sequence, and said HSV antigen is transcribed and translated in said host cell without introduction of an antimicrobial agent to lyse the bacterium to generate said immune response against HSV.

2. A method according to claim 1 which is a protective method.

3. A method according to claim 1 which is a therapeutic method.

4. A method according to claim 1, wherein said HSV antigen is a HSV-1 antigen.

5. A method according to claim 1, wherein said HSV antigen is a HSV-2 antigen.

6. A method according to claim 1, wherein at least one of said regulatory sequences is a promoter derived from an eukaryotic organism or a virus which infects eukaryotic cells and which directs transcription of said coding sequence in said host cell.

7. A method according to claim 1, wherein said bacterium is a *Salmonella, Shigella* or *Listeria* bacterium.

8. A method according to claim 1, wherein said bacterium is a bacterium that is not naturally invasive but has been altered such that it has become invasive.

9. A method according to claim 8, wherein said bacterium is an *E. coli* bacterium.

10. A method according to claim 1, wherein said composition is delivered to a mucosal surface.

11. A method according to claim 10, wherein said composition is delivered orally, intrarectally, intranasally or intravaginally, or as a respiratory spray.

12. A method according to claim 1, wherein said composition is formulated for delivery to a human host.

13. A method according to claim 1, wherein said composition is formulated for delivery to an animal host.

14. A method according to claim 13, wherein said composition is formulated for delivery to a mammalian or avian animal host.

15. A method according to claim 14, wherein said composition is formulated for delivery to a bovine, ovine, swine or equine host, or to a poultry species host.

16. A method according to claim 1, wherein said composition further comprises an agent capable of stimulating cellular immunity.

17. A method according to claim 16, wherein said agent is capable of stimulating cellular mucosal immunity.

18. A method of generating a protective immune response to a herpes simplex virus (HSV) in a human or animal host, said method comprising:

(a) providing an immunogenic composition; wherein said composition is comprised of an invasive but attenuated or non-pathogenic bacterium selected from the group consisting of *Salmonella, Shigella, Listeria* and *E. coli* bacteria; said bacterium is comprised of a coding sequence encoding a herpes simplex virus (HSV) antigen selected from the group consisting of glycoprotein D, glycoprotein H, glycoprotein B and ICP27; and said coding sequence is comprised within an expression construct and operably linked to one or more regulatory sequences and (b) administering said composition to said host such that said bacterium invades a host cell of said host selected from the group consisting of macrophages and dendritic cells and said expression construct is transferred into said host cell where said regulatory sequences direct expression of said coding sequence, and said HSV antigen is transcribed and translated in said host cell without introduction of an antimicrobial agent to lyse the bacterium to generate said prophylactic immune response against HSV.

19. A method according to claim 18, wherein said HSV antigen is from HSV-1.

20. A method according to claim 18, wherein said HSV antigen is from HSV-2.

21. A method according to claim 18, wherein at least one of said regulatory sequences is a promoter derived from a eukaryotic organism or a virus which infects eukaryotic cells and which directs transcription of said coding sequence in said host cell.

22. A method according to claim 18, wherein said composition is delivered to a mucosal surface.

23. A method according to claim 18, wherein said composition further comprises an agent capable of stimulating cellular immunity.

24. A method according to claim 23, wherein said agent is capable of stimulating cellular mucosal immunity.

* * * * *